Figure 1:
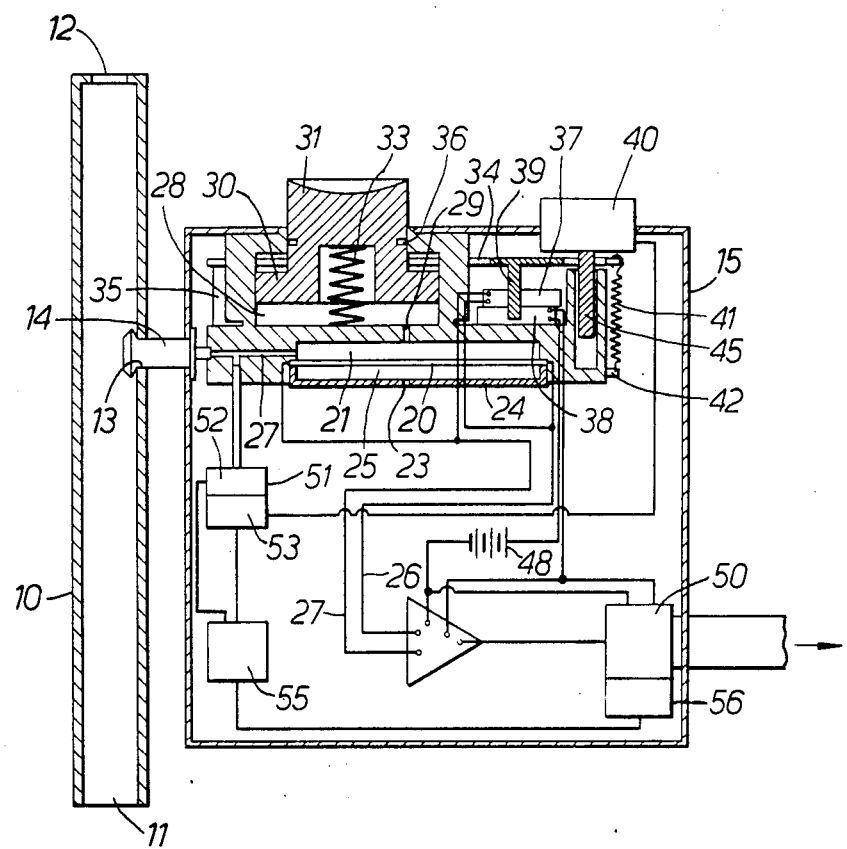

United States Patent [19]

Jones

[11] Patent Number: 4,707,336

[45] Date of Patent: Nov. 17, 1987

[54] APPARATUS FOR GAS ANALYSIS

[75] Inventor: Thomas P. Jones, Sully, United Kingdom

[73] Assignee: Lion Laboratories Limited, Barry, United Kingdom

[21] Appl. No.: 707,573

[22] Filed: Mar. 4, 1985

[30] Foreign Application Priority Data

Mar. 2, 1984 [GB] United Kingdom ................ 8405481

[51] Int. Cl.$^4$ ........................ G01N 27/46; G01N 1/24
[52] U.S. Cl. .......................................... 422/84; 73/23;
128/719; 436/132; 340/632
[58] Field of Search ................. 73/23, 27 R; 128/719,
128/730; 422/84–86; 436/132; 340/576, 632

[56] References Cited

U.S. PATENT DOCUMENTS

| | | | |
|---|---|---|---|
| 3,877,291 | 4/1975 | Hoppesch et al. | 73/27 R |
| 4,093,945 | 6/1978 | Collier et al. | 340/576 X |
| 4,132,109 | 1/1979 | VanderSyde | 73/23 |
| 4,297,871 | 11/1981 | Wright et al. | 128/719 X |
| 4,300,385 | 11/1981 | Albarda | 422/84 X |

FOREIGN PATENT DOCUMENTS 1443438 7/1976 United Kingdom .................. 73/23

Primary Examiner—Barry S. Richman
Assistant Examiner—Michael S. Gzybowski
Attorney, Agent, or Firm—Young & Thompson

[57] ABSTRACT

A breath alcohol testing instrument comprises a breathing tube (10) connected to an instrument (15) for detecting alcohol, including a sampling system comprising a spring-loaded piston (30) arranged to draw a gas sample into a sampling chamber (21) in contact with an electrochemical fuel cell (20). A pressure sensor (52) detects a predetermined breath flow rate and starts a timer (53) which after a predetermined interval actuates a solenoid (40) to release the sampler. If the suspect interrupts normal breath flow the system does not "abort". The solenoid (40) is still actuated automatically either immediately when the pressure sensor (52) indicates a predetermined drop in pressure or after the preselected time interval. Simultaneously a "test fail" signal is generated (55) and applied to a warning signal generator (56) which actuates a visible or audible warning sign to indicate a non-standard test result.

1 Claim, 3 Drawing Figures

APPARATUS FOR GAS ANALYSIS

This invention relates to apparatus for use in detecting constituents of a gas, especially expired breath, and is particularly though not exclusively applicable to alcohol breath testing equipment.

It is well known that to obtain an accurate indication of the alcohol content of the blood a breath sample should be taken from the alveolar lung passages. In practice this means that the first part of the gases exhaled from the lungs have a distorted alcohol content and should be disregarded. It is also known that the person under test may deliberately or accidentally upset the accuracy of the test by interrupting the flow of breath and possibly inhaling briefly while the test is in progress. Obviously any inhaling of fresh air which is then immediately exhaled would affect the reading of the test instrument.

In an attempt to overcome this problem it has been proposed to incorporate an automatic flow sensor which includes an element sensitive to the rate of flow and another element acting as a timer which is automatically activated when the flow rate exceeds a predetermined minimum. If the flow rate falls below this minimum the timer is re-set and the whole count must start afresh.

It has been found that for some purposes an automatic control system as described is not satisfactory. For example in some cases it may be of value to have an output reading from the sensor even though the correct test considerations have not been fulfilled, but it is nevertheless important in most applications and often a legal requirement that no alcohol breath test is acceptable until the true alveolar breath is reaching the sensor. These factors are conflicting and appear to be irreconcilable, but surprisingly the present invention is capable of providing a solution.

Broadly stated the invention consists in apparatus for detecting a constituent in a gas, comprising an input tube, an automatic gas sampler connected to the input tube, and a detector for the constituent, control means including a flow sensor responsive to the flow through the input tube, and a timer, and arranged to actuate the sampler automatically after a determined interval when a selected flow of gas has been sensed, and a signal generator for detecting any substantial interruption, reduction or reversal in the gas flow, and arranged to actuate a signal to indicate that the test has taken place under non-standard conditions.

According to a preferred feature of the invention the signal generator is arranged to operate a visual or audible warning signal, or to apply a printed warning symbol to a record sheet on which the output of the detector is also printed.

In some cases the control means is arranged to operate automatically to cause a sample of gas to be analysed, immediately any substantial interruption or reduction or reversal in gas flow occurs. Alternatively the control means may be arranged to operate automatically when the determined time interval or gas flow has passed, regardless of any interruption in flow.

Figure 2:
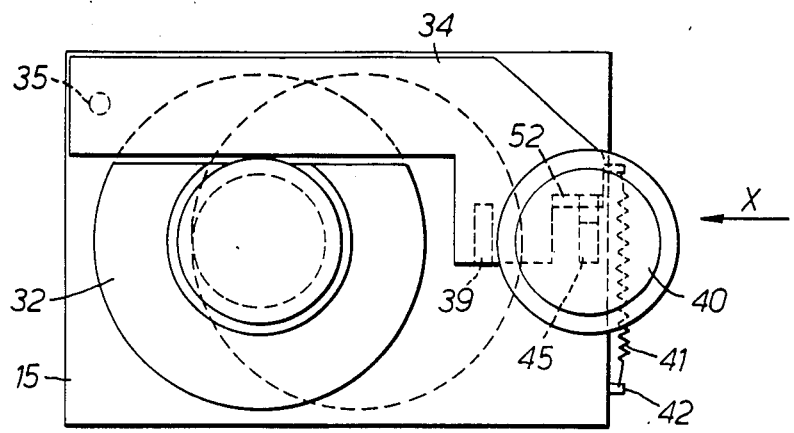
Figure 3:
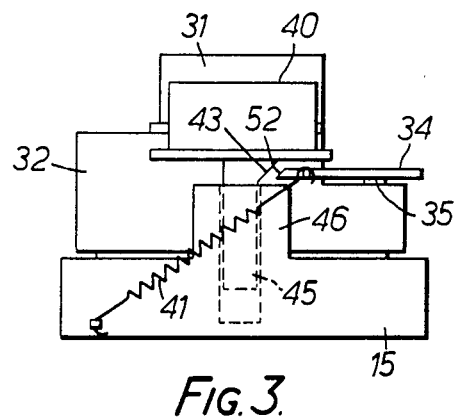

The invention may be performed in various ways and one specific embodiment with some possible modifications will now be described by way of example with reference to the accompanying drawings in which:

FIG. 1 is a diagram illustrating the main components of a breath testing apparatus according to the invention, FIG. 2 is a plan view of some of the internal components, and FIG. 3 is an end view of these components, seen in the direction of arrow X in FIG. 2.

In this example the invention is applied to a breath testing machine of the type designed to be used in a police station for providing a printed authenticated read-out of the breath alcohol content of any driver suspected of driving under the influence of alcohol. The apparatus comprises a replaceable breathing tube 10 having a mouth piece 11 and a slightly restricted opening at the opposite end 12. A lateral opening 13 is detachably connected to a short tube 14 communicating with the gas sampling and sensing system in the instrument 15. From the end of the tube 14 a small bore tube 27 leads to a chamber 21 within the body of the device. This chamber is closed by a gas sensing element which is the upper part of a comparison capsule. This has a small central opening 23 in bottom wall 24 through which atmospheric air (the comparison gas) can penetrate into another enclosed chamber 25 between the discs 20 and 24.

The sensing element 20 comprises an intermediate membrane of thin film of permeable material such as sintered glass, ceramic or synthetic plastics material, which is impregnated with a liquid or semi-solid electrolyte such as a solution of phosphoric acid and/or sodium hydroxide. The upper and lower surfaces of this membrane or film are provided with thin coatings of a precious metal such as gold, silver, platinum, palladium, ruthenium, or any metal of the platinum group or an alloy of one or more of these metals. The metal is selected for its ability to act as a catalyst in the presence of alcohol vapour to cause any alcohol vapour in chamber 21 to become oxidised on the upper surface of the detector element. Simultaneously the oxygen in the chamber 25 below the element 20 will likewise become reduced, and as a result an e.m.f. will be generated between the two metal surfaces acting respectively as anode and cathode. No external potential is applied. These two plated metal surfaces are connected respectively to a pair of insulated electrical leads 26 and 27, which are connected into the electrical circuit to be described later. The device also includes means for controlling the admission and expulsion of the gas sample into the chamber 21. This comprises a second chamber 28 connected to the chamber 21 by a small port 29 and a piston 30 integral with a button 31 projecting through an aperture in an end cap 32. A spring 33 urges this piston and button upwards. A plate type latch 34 is pivotally mounted on a pillar 35 outside this chamber and is generally L-shaped in plan view (see FIG. 2). The pivot point is at the end of the long arm which, at an intermediate point, projects inwards through a slot in the cap 32 and bears against the cylindrical surface of the button 31. It can engage in a peripheral groove 36 when the button is fully depressed downwards, to hold the piston in this position. The short arm of the latch 34 extends around the piston chamber and over the spring loaded trip levers of a pair of microswitches 37,38. It co-operates with these by means of a downward projection 39.

The outside of the short arm is connected to one end of an inclined spring 41, the other end of which is attached to a lug 42 on the body of the device. The spring urges the long arm of the latch against the push button 31. The extremity of the short arm has an inclined cam surface 52 which is engaged by a cam shoulder 43 on a stem 45 guided vertically by a hollow sleeve 46. The stem 45 is actuated automatically by a solenoid 40, and when depressed pivots the latch 34 away from the button 31 and actuates the microswitches as described below.

It will be seen that when the button 31 is depressed air in the chamber 28 is expelled through the port 29 and so expels the gas in the chamber 21 above the sensing element. When the latch 34 is released the spring 33 urges the piston 30 upwards and gas is drawn from the mouthpiece 10 through the passage 27 into the chamber 21 and also through the port 29 into the chamber 28. Since both the chamber 21 and the chamber 29 are of fixed volumetric capacity it is possible to determine accurately the volume of gas in the sample and hence to provide a consistent basis for measurement.

Referring now to the electric circuit, the first microswitch 37 is arranged when closed to short circuit the two electrode coatings of the sensing element 20. The other microswitch 38 is arranged in series with a battery 48 for energising an operational amplifier circuit 49, to which the electrode voltages are applied, and an automatic printer 50. Both these microswitches are normally open.

The piston 30 is "cocked" or set manually by depressing the button 31, which is held down by latch 34 engaging in groove 36, and is automatically released by a flow sensing device 51 at a controlled instant, so as to draw a sample of breath rapidly into the sensing chamber 21. The flow sensor 51 includes a pressure sensing device 52 and an automatic timer 53 so arranged that the timer is started automatically when the flow pressure sensor indicates that the breath pressure in the tube 27 is above a determined minimum value. The timer may be adjustable or preset, for example at an interval of, say, four seconds, so designed that after this interval the breath of a normal subject flowing through the tube 10 will be "alveolar", i.e. from the deep parts of the lungs. After the timer 53 has run its set period a signal is delivered on line 54 to the solenoid 40 arranged to trip the latch 34 and cause the sampling piston 25 to be released so as to move under the action of the spring 29 to draw the breath sample into the chamber 21.

If the suspect interrupts the flow of breath before the full 4 second internal, or "snatches" a fresh breath, the pressure of the breath in the tube 10 and passage 27 will probably fall below the minimum set pressure value at pressure senser 52 and the sensor will produce a corresponding change in output, but in this instrument the timer 53 will not be re-set automatically but will continue to operate to the end of its full set time. A "negative detector" 55 sensitive to the output of the pressure sensor 52 will however transmit a control signal to a "negative signal generator" 56 to provide a warning that the breath flow has been reduced or interrupted during the test. This negative signal may be for example a light, or alternatively or in addition it may include an extra printing element in the automatic printer 50, arranged to apply a printed warning symbol on the same printed sheet which carries the particulars of the alcohol breath contents received direct from the fuel cell 20. Likewise if the instrument includes a digital display, for example an LCD display unit arranged to indicate the sensed breath alcohol level, the signal generator 55 may be arranged to cause this display to pulse or flash, thus clearly indicating that although an alcohol reading has been taken, the conditions do not comply with police regulations. Accordingly the operator or police officer will then decide whether or not a further test is required, but nevertheless will have the benefit of the test performed by the machine. The invention may also be applied to other types of automatic testing instruments arranged to test and analyse a sample of the breath at a selected instant, not necessarily using a pressure sensor and timer 52, 53 as in the described example. For example, a thermistor circuit may be arranged to provide an equivalent delay function, related to the total flow of breath. Likewise the invention is not confined to an instrument using an electro-chemical fuel cell of the type shown at 20 in the example above. The invention is equally applicable to instruments using other types of detectors or analysers, for example heated resistors or infra-red detectors.

It will be understood that in instruments according to the invention, if the breath flow is briefly interrupted or even totally stopped in mid-test, the normal function of the control system continues and a test is taken automatically at the determined instant. This has surprising results and advantages.

In the example illustrated and described above, if there is any failure in the breath flow during the test the pressure sensor 52 senses the mal-function, but the timer 53 continues to the end of its set interval. In a possible alternative the timer is reset immediately and an immediate signal is transmitted to the solenoid 40 so that the sample is taken and the analysis performed immediately when the breath failure occurs. Simultaneously the failure is displayed by the unit 56. The automatic sampler is extremely rapid in operation and normally will take a sample of the suspect's breath even if the breath flow is completely interrupted.

I claim:

1. Apparatus for detecting alcohol in expired breath comprising a breathing tube having an input end and an output end, an automatic breath sampler connected to said tube at a position between said input and output ends, said breath sampler including a sampling chamber of predetermined volume, a detector for detecting alcohol in a breath sample within said chamber, automatic control means including a flow sensor responsive to flow through said breathing tube and at timer operatively connected to said flow sensor to actuate the sampler automatically after a predetermined interval when a selected breath flow has been sensed, sensing means for detecting any substantial interruption, reduction or reversal in said breath flow through said breathing tube, a warning signal generator responsive to said sensing means which indicates when breath flow has been substantially interrupted, reduced or reversed during a test and which sensing means is operatively connected to said sampler to cause immediate actuation thereof on receipt of said warning signal prior to the expiration of said predetermined interval.

* * * * *